United States Patent
Uttenthal et al.

(10) Patent No.: US 12,239,727 B2
(45) Date of Patent: Mar. 4, 2025

(54) COMPOSITIONS FOR USE IN THE TREATMENT OF PHOTOSENSITIVITY

(71) Applicant: RepoCeuticals A/S, Hørsholm (DK)

(72) Inventors: Lars Otto Uttenthal, Madrid (ES); Torsten Bjørn, Kvistgård (DK)

(73) Assignee: RepoCeuticals A/S, Hørsholm (DK)

( * ) Notice: Subject to any disclaimer, the term of this patent is extended or adjusted under 35 U.S.C. 154(b) by 776 days.

(21) Appl. No.: 17/296,874

(22) PCT Filed: Dec. 4, 2019

(86) PCT No.: PCT/EP2019/083610
§ 371 (c)(1),
(2) Date: May 25, 2021

(87) PCT Pub. No.: WO2020/115102
PCT Pub. Date: Jun. 11, 2020

(65) Prior Publication Data
US 2022/0016006 A1   Jan. 20, 2022

(30) Foreign Application Priority Data

Dec. 5, 2018 (DK) .......................... PA 2018 70796
Jan. 16, 2019 (DK) .......................... PA 2019 70031

(51) Int. Cl.
*A61K 8/49* (2006.01)
*A61K 8/46* (2006.01)
*A61Q 17/04* (2006.01)

(52) U.S. Cl.
CPC .............. *A61K 8/492* (2013.01); *A61K 8/46* (2013.01); *A61Q 17/04* (2013.01)

(58) Field of Classification Search
None
See application file for complete search history.

(56) References Cited

U.S. PATENT DOCUMENTS

2013/0259815 A1   10/2013   Loy et al.
2020/0100997 A1*  4/2020   Soler .................... A61K 31/593

FOREIGN PATENT DOCUMENTS

| WO | WO 98/55075 A2 | 12/1998 |
| WO | WO 2008/036979 A2 | 3/2008 |
| WO | WO 2012/143875 A1 | 4/2012 |
| WO | WO 2018/141988 A1 | 8/2018 |
| WO | WO 2018/167273 A1 | 9/2018 |

OTHER PUBLICATIONS

Akbarzadeh, Maryam et al., "Effects of combination of melatonin and laser irradiation on ovarian cancer cells and endothelial lineage viability" Lasers Med Sci, 2016, pp. 1565-1572, vol. 31.
Kleszczynski, Konrad et al., "Differential effects of melatonin as a broad range UV-damage preventive dermato-endocrine regulator" Dermato Endocrinology, Jan. 2011, pp. 27-31, vol. 3.
Vijayalaxmi et al., "Melatonin as A Radioprotective Agent: A Review" Int. J. Radiation Oncology Biol. Phys., 2004, pp. 639-653, vol. 59, No. 3.
International Search Report for PCT/EP2019/083610 dated Feb. 28, 2020.
Ranaweera, Anoma. "Radiation dermatitis." DermNet New Zealand. Available on Wayback Nov. 24, 2016. < https://web.archive.org/web/20161124021446/https://dermnetnz.org/topics/radiation-dermatitis>.
Oakley, Amanda. "Photosensitivity" DermNet New Zealand. Available on Wayback Oct. 21, 2016. <https://web.archive.org/web/20161021142223/http://www.dermnetnz.org/topics/photosensitivity/>.
Oakley, Amanda. "Photosensitivity Dermatitis" DermNet New Zealand. Available on Wayback Oct. 21, 2016. <https://web.archive.org/web/20161021133835/http://www.dermnetnz.org/cme/dermatitis/photosensitivity-dermatitis/>.

* cited by examiner

*Primary Examiner* — Nannette Holloman
(74) *Attorney, Agent, or Firm* — Knobbe Martens Olson & Bear LLP

(57) ABSTRACT

Compositions comprising melatonin and/or derivatives thereof for topical application to the skin for use in the treatment of photosensitivity of whatever cause are described.

8 Claims, No Drawings

COMPOSITIONS FOR USE IN THE TREATMENT OF PHOTOSENSITIVITY

CROSS REFERENCE TO RELATED APPLICATIONS

This application is a U.S. National Phase Application of PCT International Application Number PCT/EP2019/083610, filed on Dec. 4, 2019, designating the United States of America and published in the English language, which is an International Application of and claims the benefit of priority to Danish Patent Application No. PA 2018 70796, filed on Dec. 5, 2018, and Danish Patent Application No. PA 2019 70031, filed on Jan. 16, 2019. The disclosures of the above-referenced applications are hereby expressly incorporated by reference in their entireties.

FIELD OF INVENTION

The present invention provides compositions comprising melatonin and/or an antioxidant metabolite, derivative or analogue thereof as the essential ingredient for use when preventing and treating photosensitivity of the skin, in particular, but not exclusively, chemical photosensitivity due to the systemic administration or topical external application of chemical compounds that induce skin photosensitivity, whether this be an unwanted side effect or part of photodynamic therapy e.g. for cancerous or precancerous lesions. As such, it is relevant to the fields of dermatology, oncology and general internal medicine, and particularly relevant as an adjunct to photodynamic therapy applied to skin lesions.

BACKGROUND OF THE INVENTION

Photosensitivity and Photodynamic Therapy

The term photosensitivity is herein used to refer to various symptoms, conditions or diseases of the skin that are caused or aggravated by a lesser degree of exposure to sunlight than that which might cause similar symptoms in an average, healthy individual. The term is often used informally, as the range of responses to sunlight exposure varies widely between healthy individuals. For example, individuals with very white skin that does not tan easily, who are more susceptible to sun scalding on minor exposure to sunlight, may be called "photosensitive" in comparison with darker-skinned individuals who may be relatively resistant to sun scalding. For the avoidance of ambiguity, any acute reddening, swelling and painful inflammation of the skin following sunlight exposure, which is often called "sunburn", is herein referred to as "sun scalding", whereas the terms "sunburn" or "sunburnt" are reserved to refer to the longer-term tanning/darkening of the skin due to increased pigmentation as a result of successive periods of exposure to sunlight. Sun scalding is the prime indicator of "phototoxicity". This may sometimes be followed by an allergic, delayed hypersensitivity reaction to compounds formed in the skin during the sun exposure, this being known as "photoallergy" and classified as a type of "photodermatitis". In general, a rash due to photosensitivity is a "photodermatosis"; if eczematous, it is a "photodermatitis". A further term used is "photoexacerbation", referring to the exacerbation of a pre-existing skin condition by exposure to sunlight.

Photosensitivity may have many underlying causes: rare congenital or genetic disorders, metabolic disorders such as various types of porphyria in which phototoxic porphyrins accumulate in skin cells, primary photodermatoses, a large number of photoexacerbated dermatoses, and exogenous photodermatoses caused by photosensitizing drugs or chemicals. Immunosuppressed individuals, such as patients that have undergone organ transplantation or patients with a chronic lymphoid malignancy may also become very photosensitive. The chemical photosensitivity induced by the administration of various drugs and by the deliberate use of photosensitizers in photodynamic therapy of cancerous of precancerous lesions is of particular interest because it represents a side effect of therapeutic intervention, placing a particular obligation on health care providers to avoid, minimize or treat it. In the following, the term "photosensitivity" includes any increased susceptibility of the skin to the immediate or long-term harmful effects of exposure to light of the ultraviolet (UV) or visible spectrum, said long-term effects including the development of skin cancers or precancerous skin diseases, that results from a therapeutic intervention of any type.

A common link in the pathogenesis of skin reactions to sunlight is the production of free radicals in the living skin cells, e.g. keratinocytes and fibroblasts, which, when their production exceeds the intrinsic free radical scavenging capacity of the cells, have damaging effects on cellular DNA and cell structures, leading eventually to cell death, e.g. by apoptosis or mitochondrially induced mechanisms. The cellular damage triggers an inflammatory response. This is thought to underlie the pathology of the acute phototoxic reaction of sun scalding, which may then progress to the later manifestations of photosensitivity. Chemical photosensitivity is caused by the presence of compounds with chromophores that absorb energy from the incident light and are themselves converted into free radicals, or catalyze the generation of free radicals in the cellular cytoplasm. Depending on the characteristics of the chromophore, the activating light may be UVB (of wavelength 290-320 nm), UVA (of wavelength 320-400 nm), or may even be light within the visible spectrum.

Photodynamic therapy seeks to exploit chemical photosensitivity by employing specific photosensitizing agents which are intended to be preferentially absorbed by the cells of the lesion to be treated, usually cancerous or precancerous lesions. Light of the appropriate wavelength is then applied to kill the cells of the lesion by the intracellular generation of free radicals. Depending on the part of the body to be treated, the photosensitizing agent is either administered systemically (i.e. intravenously) or, for skin lesions, is applied topically to the lesion and its immediately surrounding area. After a certain "drug-to-light" interval to allow the cancer cells to absorb the photosensitizer, which may be from a few hours to two days, the light is applied. However, the absorption of the photosensitizers used is by no means absolutely specific to the cells to be treated, so that the treatment can leave the patient in a highly photosensitive state for some considerable time before the photosensitizer is eliminated from the normal skin cells.

Treatment of photosensitivity is based chiefly on the avoidance of exposure to sunlight or even some types of artificial light, dressing so as not to leave any significant skin area uncovered (including even cloth coverage or masking of the face), treating any underlying disease, if possible, and of course minimizing exposure to any photosensitizing agents. Avoidance of light exposure may impose a severe impairment to the patient's quality of life. Sunscreens are regarded as a necessary aid to reduce the effects of inevitable sun exposure, but their contribution to treatment is not seen to be very efficacious, and they will not be effective if the photosensitivity is towards light in the visible spectrum. Sometimes corticosteroids are applied topically to reduce the inflammatory and immune components of any photosensitivity response. Overall, there is a medical need for more effective treatment of photosensitivity that might improve resistance to the noxious effects of light exposure and improve the quality of life for many affected patients.

SUMMARY OF THE INVENTION

The present invention provides dermatological compositions comprising melatonin and/or an antioxidant metabolite, derivative or analogue thereof (hereinafter called melatonin-related compounds) to improve the prevention and treatment of photosensitivity by the direct topical administration to the affected skin in the form of a liquid or semiliquid dermatological preparation. The compositions also comprise dimethyl sulfoxide (DMSO) to dissolve the melatonin or melatonin-related compounds and prevent its breakdown on storage, as well as to enhance the penetration of the melatonin or melatonin-related compounds into skin cells. The compositions may also optionally contain broad-spectrum sunscreen agents that are not in themselves known to act as photosensitizers. The advantage of the present invention is that the melatonin or melatonin-related compounds is/are delivered at high dose directly to the cells that need protection from free radical damage due to light exposure. The melatonin or melatonin-related compounds acts as a highly effective free radical scavenger to revert the effects of any photosensitizing agent present in the cells, such as porphyrins in cases of certain types of porphyria, photosensitizing agents administered in connection with photodynamic therapy, photosensitizing medication administered for other therapeutic purposes, or exposure to photosensitizing chemical agents in general. Whereas sunscreens act by absorbing incident UV light, but not light of the visible spectrum, the melatonin or melatonin-related compounds act by greatly augmenting the free radical scavenging capacity of the cells, so that they are protected against the cell-damaging effects of the incident light, not against the entry of the light itself.

Accordingly, the present invention provides a composition comprising a) melatonin and/or a derivative or analogue thereof, according to the formula

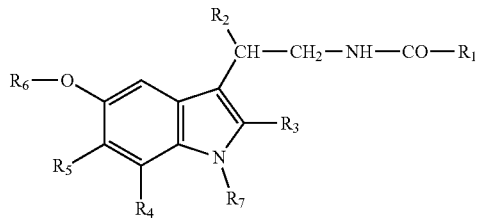

(I)

in which $R_1$ represents H, a linear or branched $C_1$-$C_4$ alkyl group or a $C_1$-$C_4$ alkoxy group, $R_2$ represents H or a $C_1$-$C_4$ alkyl group, $R_3$ represents H, a methyl group or a halogen atom, $R_4$ represents H or a halogen atom, $R_5$ represents H or a halogen atom, $R_6$ represents H or a linear or branched $C_1$-$C_4$ alkyl group, $R_7$ represents H, a linear or branched $C_1$-$C_4$ alkyl group, a —C(=O)—O—$R_a$ group or a —C(=O)—N(H)—$R_a$ group wherein $R_a$ is a linear or branched $C_1$-$C_4$ alkyl group, the —$CH_2$—NH—C(=O)—$R_1$ side chain is extended by duplicating, triplicating or quadruplicating the —$CH_2$— group, or pharmaceutically acceptable salts of such derivatives; and/or the melatonin metabolites $N^1$-acetyl-$N^2$-formyl-5-methoxykynuramine (AFMK) or N-acetylserotonin (NAS), and b) dimethyl sulfoxide (DMSO), for use in the treatment of skin photosensitivity, wherein the composition is to be applied topically.

In one embodiment, the composition for use according to the invention further comprises one or more sunscreen agents chosen from a list comprising Avobenzone, diethylamino hydroxybenzoyl hexyl benzoate, menthyl anthranilate, Homosalate, and Iscotrizinol.

In another embodiment, the composition for use according to the present invention further comprises alpha-tocopherol as a synergically acting antioxidant.

In another embodiment, the composition for use according to the present invention the composition is formulated as a liquid solution, emulsion or suspension, a spray, a lotion, gel, cream, salve, ointment or paste.

In another embodiment, the composition for use according to the present invention the concentration of melatonin or antioxidant metabolite, derivative or analogue thereof is from 0.1% (w/w) to 15% (w/w) and the concentration of DMSO is from 5% (w/w) to 50% (w/w).

In another embodiment, the skin photosensitivity to be treated is chemical photosensitivity due to the administration of a photosensitizing agent.

In another embodiment, the skin photosensitivity is photosensitivity persisting after a session of photodynamic therapy.

In another embodiment, the skin photosensitivity is any increased susceptibility of the skin to the immediate or long-term harmful effects of exposure to light of the UV or visible spectrum, said long-term effects including the development of skin cancers or precancerous skin diseases, that results from a therapeutic intervention of any type.

In the following detailed description of the invention, details of the scope of the invention will be given, together with details of the practical performance of the invention.

DETAILED DESCRIPTION OF THE INVENTION

In describing the embodiments of the invention, specific terminology will be resorted to for the sake of clarity. However, the invention is not intended to be limited to the specific terms so selected, and it is understood that each specific term includes all technical equivalents which operate in a similar manner to accomplish a similar purpose.

When describing the embodiments of the present invention, the combinations and permutations of all possible embodiments have not been explicitly described.

Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and "comprises" herein are intended by the inventors to be optionally substitutable with the terms "consisting of", "consist of" and "consists of", respectively, in every instance.

As used herein, the singular forms "a", "an" and "the" are intended to include the plural forms as well, unless the context clearly indicates otherwise.

Active Ingredients

The principal active ingredient of the compositions of the invention is melatonin or an antioxidant metabolite, derivative or analogue thereof. A further active ingredient is DMSO, and additional, optional active ingredients are sunscreen agents and antioxidants acting synergically with melatonin and melatonin-related components.

Melatonin

Melatonin (N-acetyl-5-methoxytryptamine) is a hormone produced by the pineal gland in human beings and other mammals by enzymatic modification of the amino acid tryptophan. Melatonin is involved in maintaining the circadian rhythm of various biological functions, being secreted in hours of darkness and acting on high-affinity melatonin $G_i$-coupled transmembrane receptors MT1 and MT2, which are widely distributed in many cells and tissues of the body. At the same time melatonin acts at supraphysiological concentrations as a powerful antioxidant and free radical scavenger for reactive oxygen species (ROS) and reactive nitrogen species (RNS) (Gomez-Moreno et al 2010). Melatonin can also activate cytoprotective antioxidant enzymes such as copper-zinc and manganese superoxide dismutases (CuZnSOD and MnSOD) and glutathione peroxidase (Rodriguez et al 2004). In addition, melatonin has anti-inflammatory effects to prevent the upregulation or cause the down-regulation of the expression of nuclear factor kappa B (NF-κB) and pro-inflammatory cytokines such as tumor necrosis factor alpha (TNF-α) and interleukin 1 beta (IL-1β).

Melatonin as an agent to protect against radiation injury: Because of melatonin's efficiency as a free radical scavenger, especially of hydroxyl radicals (Tan et al 1993) and ROS, it has been proposed as an agent to protect against radiation injury, including photochemical injury, to cells and tissues. Melatonin has been demonstrated to protect against the adverse effects of all relevant wavelengths ionizing radiation from ultraviolet through x-rays to gamma rays. The results of such studies have been reviewed by Vijayalaxmi et al (2004). Melatonin has been shown to protect skin cells against the harmful effects of UV light, as has been reviewed by Kleszczynski et al (2011). However, there have been no studies of melatonin as an agent to treat photosensitivity.

The above considerations indicate that a major part of the protective effect of melatonin against damage from incident light depends on the intracellular presence of melatonin at the time of radiation. This would be consistent with the near instantaneous intracellular production of free radicals as a result of the entry of light and their initiation of DNA and mitochondrial damage leading to cell death. Melatonin acts as a potent free radical scavenger and may thus prevent or reduce the initiation of cell damage in the phototoxic sun-scalding phase of photosensitivity. In this sense, melatonin can be called a powerful "photodesensitizer". Melatonin then also activates cytoprotective enzymes and down-regulates pro-inflammatory cytokines, providing a longer-term protection against the later consequences of photosensitivity.

There has been some concern that pre-treatment with systemically administered melatonin might also diminish the effectiveness of radiotherapy to kill tumor cells. While this has not been confirmed in clinical studies, and melatonin shows an independent anti-cancer activity, it seems evident that melatonin should not be used simultaneously with photodynamic therapy for cancerous or precancerous lesions. It would be contradictory to use both photosensitizers and a powerful photodesensitizer simultaneously. Melatonin can, however, be used to treat the residual photosensitization of normal skin once a session photodynamic therapy has been completed.

Melatonin Metabolites, Derivatives and Analogues

Many chemical derivatives of melatonin, including breakdown products and natural metabolites of melatonin, retain the antioxidant and free-radical scavenging properties of the parent molecule. This makes melatonin a more effective antioxidant than other natural antioxidants such as vitamins C and E (cited by Reiter et al 2007). However, these vitamins show synergy with melatonin with respect to antioxidant activity. In non-hepatic tissues, the reaction of melatonin with two hydroxyl radicals yields the metabolite cyclic 3-hydroxymelatonin (C3-OHM), which undergoes further oxidation by two hydroxyl radicals to break the indole ring and form $N^1$-acetyl-$N^2$-formyl-5-methoxykynuramine (AFMK) (Tan et al 1993; Reiter et al 2007). C3-OHM is therefore also an effective antioxidant and hydroxyl radical scavenger. The reaction of melatonin with the hydroxyl radical precursor, hydrogen peroxide, similarly leads to production of AFMK. AFMK is also a reducing agent, capable of donating electrons to detoxify radical species, and has been shown to preserve the integrity DNA exposed to oxidizing agents. The action of aryl formamidase or catalase on AFMK produces $N^1$-acetyl-5-methoxykynuramine (AMK), which is an even more effective scavenger of hydroxyl radicals and reactive nitrogen species, protecting proteins from oxidative destruction. In this process, 3-acetamidomethyl-6-methoxycinnolinone (AMMC) or 3-nitro-AMK (AMNK) are formed.

The liver is the principal site of the classically reported metabolic pathway for melatonin. This consists chiefly of 6-hydroxylation by the cytochromes P450 CYP1A1, CYP1A2, and CYP1B1, and the formation of the minor metabolite N-acetylserotonin by CYP2C19. The main product 6-hydroxymelatonin (6-OHM) is then conjugated at the hydroxyl group to form the 6-OHM glucuronide or 6-OHM sulfate. 6-OHM is an effective free radical scavenger in a variety of situations, but is also reported to show pro-oxidant effects in others. Its status as an antioxidant thus remains equivocal (Maharaj et al 2007).

N-acetylserotonin (NAS) is not only the immediate biosynthetic precursor but also a minor metabolite of melatonin. Like 6-OHM, it is conjugated to form the glucuronide or sulfate. Its protective effect against oxidative damage in certain model systems is reportedly 5 to 20 times as strong as that of melatonin (Oxenkrug 2005).

Melatonin can also be chemically modified by introducing chemical groups at one or more of any of its constituent atoms susceptible of such modification or by introducing such groups in de novo synthesis of melatonin analogues or derivatives. Such modifications, which do not alter the fundamental indole structure of melatonin, are herein called derivatives. The fundamental indole structure of melatonin can also be modified by substituting other bicyclic aromatic structures. Such modifications are herein called analogues, which may also have different chemical side groups removed, introduced or modified. Many such analogues and derivatives have been prepared, but most of them have not been tested for their antioxidant or free-radical scavenging properties.

Antioxidant metabolites of melatonin: Of those described above, only AFMK and NAS are suitable for use in compositions of the invention. C3-OHM and AMK are unsuitable because of their instability and the effects of 6-OHM are equivocal.

Antioxidant melatonin derivatives: The chemical structure of melatonin can be represented as in Figure (I), in which sites suitable for chemical modification by the substitution of different chemical groups have been indicated by $R_1$, $R_2$, $R_3$, $R_4$, $R_5$ and $R_6$. These numbers do not correspond to the conventional numbering of positions in the indole ring of melatonin.

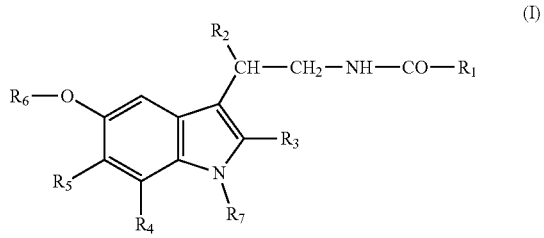

(I)

In native melatonin, $R_1$ and $R_6$ represent $CH_3$, while $R_2$, $R_3$, $R_4$, $R_5$ and $R_7$ represent H.

Antioxidant melatonin derivatives may comprise, as non-exclusive examples, those in which
- $R_1$ represents H, a linear or branched $C_1$-$C_4$ alkyl group or a $C_1$-$C_4$ alkoxy group,
- $R_2$ represents H or a $C_1$-$C_4$ alkyl group,
- $R_3$ represents H, a methyl group or a halogen atom,
- $R_4$ represents H or a halogen atom,
- $R_5$ represents H or a halogen atom,
- $R_6$ represents H or a linear or branched $C_1$-$C_4$ alkyl group,
- $R_7$ represents H, a linear or branched $C_1$-$C_4$ alkyl group, a —C(=O)—O—$R_a$ group or a —C(=O)—N(H)—$R_a$ group, wherein $R_a$ is a linear or branched $C_1$-$C_4$ alkyl group, the —$CH_2$—NH—C(=O)—$R_1$ side chain is extended by duplicating, triplicating or quadruplicating the —$CH_2$— group, or pharmaceutically acceptable salts of such derivatives.

Dimethyl Sulfoxide (DMSO)

DMSO (($CH_3$)$_2$SO), molecular weight 78.1 g/mol, is a colorless polar aprotic solvent for both polar and nonpolar compounds and is completely miscible with water and a wide range of organic solvents. It is well known as a solvent or solubilizer for melatonin. The solubility of melatonin in DMSO at room temperature may be as high as 232 g/L or higher. DMSO shows low toxicity, the median lethal dose being higher than that of ethanol (DMSO: $LD_{50}$ oral, rat, 14.5 g/kg; ethanol: $LD_{50}$ oral, rat, 7.06 g/kg). DMSO penetrates the skin and other epithelia without damaging them and can carry other compounds dissolved in it into the underlying cells and tissues. DMSO has been used in human subjects as a topical analgesic, a vehicle for the topical application of pharmaceuticals e.g. as a component of a transdermal drug delivery systems, as an anti-inflammatory agent, and as an antioxidant. DMSO has been approved by the U.S. Food and Drug Administration (FDA) for the symptomatic treatment of interstitial cystitis, in which 50% (w/w) aqueous DMSO is instilled into the urinary bladder. DMSO has also been described as having a radioprotective effect, and has, for example been used as a free-radical scavenging, antioxidant treatment for radiation cystitis (Shirley et al 1978). In the compositions of the present invention, DMSO is used as a solvent and stabilizer of melatonin and melatonin-related components, and for its property of promoting the penetration of melatonin into the skin, where it also acts as an analgesic and may itself exert a protective effect through its action as a free radical scavenger.

Sunscreen Agents

Widely used sunscreen agents (referred to as "sunscreens") may form part of the compositions of the present invention. Their purpose is to absorb a portion of the UV light incident on the skin cells during exposure to sunlight, and hence reduce the formation of intracellular free radicals which initiate the photosensitivity reaction, decreasing the burden on the free radical scavenging activity of the melatonin or melatonin-related component. Many sunscreens have absorption maxima that confine their activity to the UVB range, which is inadequate to provide effective cover for photosensitivity to longer wavelengths of light. Some protection against light of these wavelengths is provided by the broad-spectrum sunscreens that have higher absorption in the UVA range. However, even these sunscreens will not protect against light of the visible spectrum (e.g. red or blue light), which will activate the photosensitizers commonly used in photodynamic therapy. In the choice of sunscreens, preference is given to those agents that do not break down into photosensitizing compounds or allergens.

UVA sunscreen agents that may be used include: Avobenzone, diethylamino hydroxybenzoyl hexyl benzoate, menthyl anthranilate.

UVB sunscreen agents that may be used include: Homosalate, Iscotrizinol (which also filters out some UVA).

Synergically Acting Antioxidants

The present invention also provides compositions comprising melatonin or an antioxidant analogue or metabolite thereof together with a synergically acting antioxidant such as the alpha-tocopherol component of vitamin E. Other components of vitamin E, and compounds such as coenzyme Q10, alpha-lipoic acid or vitamin C are other antioxidants that might be used as additional antioxidants. These substances are soluble in DMSO in their non-derivatized forms.

Formulations

The compositions of the present invention may be in the form of a liquid solution, emulsion or suspension, a spray, a lotion, gel, cream, salve, ointment, or paste, which may be applied directly to the skin that is exposed to light.

The formulation typically contains from 1 mg to 150 mg of melatonin or antioxidant metabolite, derivative or analogue thereof per gram of formulated composition (i.e. 0.1% (w/w) to 15% (w/w)). The content of DMSO of the formulated composition is from 5% (w/w) to 50% (w/w). If sunscreen agents are added, they are chosen from the following list, which also provides the maximum concentration of the agent in the formulated composition: Avobenzone (3% w/w), diethylamino hydroxybenzoyl hexyl benzoate (10% w/w), menthyl anthranilate (5% w/w), Homosalate (15% w/w), Iscotrizinol (10% w/w). If alpha-tocopherol is added, its maximum concentration in the formulated composition is 20 mg/g, i.e. 2% (w/w).

In a preferred embodiment, the formulation is made up as a lotion or soft, readily spreadable cream, using any suitable basic dermatological lotion or cream formulation known in the art as a basis for the final formulated composition.

An embodiment of the above formulation comprises melatonin 2.5% (w/w) and DMSO 15% (w/w) formulated as a cream.

Solutes that may be added to the water in the formulated composition include pH-adjusting agents such as hydrochloric acid, sodium hydroxide and biocompatible buffering agents, non-limiting examples being sodium dihydrogen phosphate and disodium hydrogen phosphate, sodium carbonate and bicarbonate. Tonicity-adjusting agents, such as for example sodium chloride or calcium chloride, may also be added, as well as suitable preservative agents such as methyl and/or propyl parahydroxybenzoate.

Administration

Administration of an effective amount of the composition is by topical application to the skin that is likely to be exposed to light, excluding any cancerous or precancerous skin lesion that is to be treated or has been treated by photodynamic therapy, and an area of skin within 20 mm of the edge of such lesion. Administration is stopped 24-48 hours before any photosensitizer is administered for photodynamic therapy, and is restarted 24-48 hours after a session of photodynamic therapy has been completed.

Indications

1. Photosensitivity of any etiology.
2. Chemical photosensitivity due to exposure to photosensitizing chemicals, including the administration of photosensitizing medicines and the specific administration of photosensitizing agents in connection with photodynamic therapy.
3. Photosensitivity associated with any form of immunosuppression or chronic lymphoid malignancy.
4. Any increased susceptibility of the skin to the immediate or long-term harmful effects of exposure to light of the ultraviolet (UV) or visible spectrum, said long-term effects including the development of skin cancers or precancerous skin diseases, that results from a therapeutic intervention of any type.

Dose and Dosage Regimens

By "effective amount" of the pharmaceutical compositions of the present invention is meant a dose, which, when administered to a subject in need thereof, achieves a concentration of melatonin and/or a derivative, analogue or metabolite thereof which has a beneficial biological effect, i.e. by preventing or reducing photosensitivity of the skin. Such an effective amount may be determined by physicians of ordinary skill in the art attending patients with photosensitivity due to a medical condition, or residual photosensitivity induced in relation to photodynamic therapy.

The effective amounts and dosages of the ingredients of the composition are not determined in relation to body weight or body surface area, because the treatment is local to the skin that is subject to exposure to light.

The effective amount of melatonin or an analogue, derivative or metabolite thereof for a single dose of skin application may be from 0.025 mg to 0.5 mg per square centimeter of skin.

The effective dose is preferably applied to the skin once or twice daily to cover the period of expected maximum exposure to light. If the composition is used in relation to photodynamic therapy, the first effective dose is applied no sooner than 24 hours after the therapy session has been completed, and may also be given up to twice daily between photodynamic therapy sessions, the last dose being given no later than 48 hours before the administration of photosensitizer for the photodynamic therapy session. The duration of treatment may be from one week to 12 months after a session of photodynamic therapy, at the discretion of the attendant clinician. Treatment may be interrupted to ascertain whether it is still necessary, and restarted if photosensitivity is still present.

REFERENCES

Gomez-Moreno G, Guardia J, Ferrera M J, Cutando A, Reiter R J (2010) Melatonin in diseases of the oral cavity. Oral Dis 16:242-247.

Kleszczynski K, Hardkop L H, Fischer T W (2011) Differential effects of melatonin as a broad range U V-damage preventive dermato-endocrine regulator. Dermatoendocrinol 3:27-31.

Maharaj D S, Glass B D, Daya S (2007) Melatonin: new places in therapy. Biosci Rep 27:299-320.

Oxenkrug G (2005) Antioxidant effects of N-acetylserotonin: possible mechanisms and clinical implications. Ann N Y Acad Sci 1053:334-347.

Reiter R J, Tan D X, Terron M P, Flores L J, Czarnocki Z (2007) Melatonin and its metabolites: new findings regarding their production and their radical scavenging actions. Acta Biochim Pol 54:1-9.

Rodriguez C, Mayo J C, Sainz R M, Antolin I, Herrera F, Martin V, Reiter R J (2004) Regulation of antioxidant enzymes: a significant role for melatonin. J Pineal Res 36:1-9.

Shirley S W, Stewart B H, Mirelman S (1978) Dimethyl sulfoxide in treatment of inflammatory genitourinary disorders. Urology 11:215-220.

Tan D X, Chen L D, Poeggeler B, Manchester L C, Reiter R J (1993) Melatonin: a potent, endogenous hydroxyl radical scavenger. Endocrine J 1:57-60.

Vijayalaxmi, Reiter R J, Tan D X, Herman T S, Thomas C R Jr (2004) Melatonin as a radioprotective agent: a review. Int J Radiat Oncol Biol Phys 59:639-653.

The invention claimed is:

1. A method of treating skin photosensitivity of a subject in need thereof comprising topically administering to said subject a composition comprising
   melatonin
   and
   dimethyl sulfoxide (DMSO).

2. The method of claim 1, further comprising administering to said subject one or more sunscreen agents selected from avobenzone, diethylamino hydroxybenzoyl hexyl benzoate, menthyl anthranilate, homosalate, or Iscotrizinol.

3. The method of claim 1, further comprising administering to said subject alpha-tocopherol.

4. The method of claim 1, wherein the composition is formulated as a liquid solution, emulsion, suspension, spray, lotion, gel, cream, salve, ointment or paste.

5. The method of claim 1, wherein the concentration of melatonin is from 0.1% (w/w) to 15% (w/w) and the concentration of DMSO is from 5% (w/w) to 50% (w/w).

6. The method of claim 1, wherein the skin photosensitivity is chemical photosensitivity due to the administration of a photosensitizing agent.

7. The composition of claim 1, wherein the skin photosensitivity is photosensitivity persisting after a session of photodynamic therapy.

8. The method of claim 1, wherein the skin photosensitivity is any increased susceptibility of the skin to the immediate or long-term harmful effects of exposure to light of the ultraviolet or visible spectrum, said long-term effects including the development of skin cancers or precancerous skin diseases, that results from a therapeutic intervention of any type.

* * * * *

UNITED STATES PATENT AND TRADEMARK OFFICE
CERTIFICATE OF CORRECTION

| | |
|---|---|
| PATENT NO. | : 12,239,727 B2 |
| APPLICATION NO. | : 17/296874 |
| DATED | : March 4, 2025 |
| INVENTOR(S) | : Lars Otto Uttenthal |

It is certified that error appears in the above-identified patent and that said Letters Patent is hereby corrected as shown below:

In the Specification

Column 6, Line 24-34 (approx.), delete "of AFMK. AFMK is also a reducing agent, capable of donating electrons to detoxify radical species, and has been shown to preserve the integrity DNA exposed to oxidizing agents. The action of aryl formamidase or catalase on AFMK produces N1-acetyl-5-methoxykynuramine (AMK), which is an even more effective scavenger of hydroxyl radicals and reactive nitrogen species, protecting proteins from oxidative destruction. In this process, 3-acetamidomethyl-6-methoxycinnolinone (AMMC) or 3-nitro-AMK (AMNK) are formed." and insert -- of AFMK. AFMK is also a reducing agent, capable of donating electrons to detoxify radical species, and has been shown to preserve the integrity DNA exposed to oxidizing agents. The action of aryl formamidase or catalase on AFMK produces N1-acetyl-5-methoxykynuramine (AMK), which is an even more effective scavenger of hydroxyl radicals and reactive nitrogen species, protecting proteins from oxidative destruction. In this process, 3-acetamidomethyl-6-methoxycinnolinone (AMMC) or 3-nitro-AMK (AMNK) are formed. --.

Signed and Sealed this
Seventeenth Day of June, 2025

Coke Morgan Stewart
*Acting Director of the United States Patent and Trademark Office*